United States Patent
Chakravarthy (10) Patent No.: US 12,036,400 B2
(45) Date of Patent: Jul. 16, 2024

(54) MEDICAL ANCHORING APPARATUS

(71) Applicant: Accufix Medical LLC, San Diego, CA (US)

(72) Inventor: Krishnan Vijayaraghavan Chakravarthy, San Diego, CA (US)

(73) Assignee: Accufix Medical LLC

( * ) Notice: Subject to any disclaimer, the term of this patent is extended or adjusted under 35 U.S.C. 154(b) by 0 days.

(21) Appl. No.: 18/496,958

(22) Filed: Oct. 30, 2023

(65) Prior Publication Data

US 2024/0139501 A1    May 2, 2024

Related U.S. Application Data

(60) Provisional application No. 63/420,081, filed on Oct. 28, 2022.

(51) Int. Cl.

| | |
|---|---|
| *A61N 1/04* | (2006.01) |
| *A61L 31/02* | (2006.01) |
| *A61L 31/16* | (2006.01) |
| *A61N 1/05* | (2006.01) |
| *A61N 1/36* | (2006.01) |

(52) U.S. Cl.
CPC .......... *A61N 1/0472* (2013.01); *A61L 31/022* (2013.01); *A61L 31/16* (2013.01); *A61N 1/0558* (2013.01); *A61L 2300/104* (2013.01); *A61L 2300/404* (2013.01); *A61L 2400/12* (2013.01);
(Continued)

(58) Field of Classification Search
CPC ................................................. A61N 1/36017
See application file for complete search history.

(56) References Cited

U.S. PATENT DOCUMENTS

| | | | | |
|---|---|---|---|---|
| 4,926,878 A | * | 5/1990 | Snedeker | A61N 1/0492 607/152 |
| 7,343,205 B1 | * | 3/2008 | Pianca | A61N 1/0539 607/45 |
| 2007/0068526 A1 | * | 3/2007 | Lang | A61M 16/0057 128/204.22 |

(Continued)

OTHER PUBLICATIONS

Osborne MD, Ghazi SM, Palmer SC, Boone KM, Sletten CD, Nottmeier EW. Spinal cord stimulator—trial lead migration study. Pain Med. Feb. 2011;12(2):204-8. doi: 10.1111/j.1526.
(Continued)

*Primary Examiner* — Alyssa M Alter
(74) *Attorney, Agent, or Firm* — Jason C. Cameron (57) ABSTRACT

A medical anchoring apparatus is disclosed. The apparatus includes an omega-shaped anchoring element. A proximal end of the omega-shaped anchoring element has a primary inlet groove for the receiving end of a lead, while a distal end of the omega-shaped anchoring element includes a stopper element and an outlet groove for protruding lead. A nanosilver antimicrobial foam coupled beneath the distal end of the omega shaped anchoring element at a lead entry point of a skin area of a subject around the outlet groove. The apparatus employs single coated nonwoven porous acrylic adhesive, which adheres to the skin of the patient. The omega shaped anchoring element helps manage lead displacement, and secure while allowing for predefined lead migration and lead management. The nanosilver antimicrobial foam is configured with silver particles. The medical anchoring apparatus is used to secure leads that may migrate through the patient's skin into the body.

17 Claims, 7 Drawing Sheets

(52) U.S. Cl.
CPC ........ *A61N 1/0456* (2013.01); *A61N 1/36021* (2013.01)

(56) References Cited

U.S. PATENT DOCUMENTS

2019/0246972 A1* 8/2019 Burns .................... A61B 5/447

OTHER PUBLICATIONS

Jeon YH. Spinal cord stimulation in pain management: a review. Korean J Pain. Jul. 2012;25(3):143-50. doi: 10.3344/kjp.2012.25.3.143. Epub Jun. 28, 2012. PMID: 22787543; PMCID.

Hasoon J. Lead migration in spinal cord stimulation with loss of pain coverage in a CRPS patient. Saudi J Anaesth. Apr.-Jun. 2020;14(2):280-281. doi: 10.4103/sja.SJA_47_20. E.

Esomonu C, Hagedorn JM. Teaching Points: Overview of Spinal Cord Stimulation Lead Migration. Pain Med. Feb. 23, 2021;22(2):520-522. doi: 10.1093/pm/pnaa328. PMID: 33155048.

Malinowski MN, Kim CH, Deer TR. Complications of spinal cord stimulation. In: Krames ES, Peckham PH, Rezai AR, eds. Neuromodulation: Comprehensive Textbook of Principles, T.

Eldabe S, Buchser E, Duarte RV. Complications of Spinal Cord Stimulation and Peripheral Nerve Stimulation Techniques: A Review of the Literature. Pain Med. Feb. 2016;17(2):3.

Timothy R. Deer, MD, C. Douglas Stewart, PA/C, MBA, Complications of Spinal Cord Stimulation: Identification, Treatment, and Prevention, Pain.

Kim DD, Vakharyia R, Kroll HR, Shuster A. Rates of lead migration and stimulation loss in spinal cord stimulation: a retrospective comparison of.

Mekhail NA, Mathews M, Nageeb F, Guirguis M, Mekhail MN, Cheng J. Retrospective review of 707 cases of spinal cord stimulation: indications.

Jenkinson RH, Wendahl A, Zhang Y, Sindt JE. Migration of Epidural Leads During Spinal Cord Stimulator Trials. J Pain Res. Sep. 2022.

* cited by examiner

MEDICAL ANCHORING APPARATUS

CROSS-REFERENCE TO RELATED APPLICATIONS

The present application claims the benefit of priority from U.S. provisional patent application Ser. No. 63/420,081, filed on Oct. 28, 2022 and titled "SYSTEMS, METHODS, AND DEVICES FOR LEAD ANCHORING" with the above-identified application fully incorporated herein by reference.

TECHNICAL FIELD

Embodiments of the present disclosure generally relate to anatomical stimulating structures and more particularly to a medical anchoring apparatus.

BACKGROUND

Generally, spinal cord stimulation (SCS) achieves pain relief by delivering therapeutic levels of electrical current, utilizing a range of pulse forms, pulse widths, amplitudes, and frequencies, specifically targeting a particular segment of the spinal cord. A percutaneous method, which emerged in the early 1970s for the placement of SCS electrodes, has enabled clinicians to conduct screening trials aimed at identifying potential candidates for permanent implantation. The primary objectives of these SCS trials may be twofold to assess the extent of pain relief experienced by the patient and to accurately pinpoint the site of maximal stimulation.

Ideally, the trial therapy spans a duration of 3 to 7 days, and in certain regions, it can extend up to 30 days to evaluate the patient's pain relief. A successful trial necessitates the demonstration of a minimum 50% reduction in baseline pain scores or a 50% reduction in analgesic consumption, coupled with enhanced patient satisfaction and improved functionality. The SCS trials exhibit varying degrees of success, and several other factors may contribute to their failure. The most significant factors include improper placement of the lead and lead migration. Notably, lead migration stands out as the most frequently reported complication in SCS trials, occurring at an incidence rate of 13.2%. The cylindrical design of the leads used for percutaneous electrode placement lends itself to longitudinal electrode migration.

Conventionally, various anchoring methods have been devised to minimize lead migration during extended trials, and these methods have shown varying degrees of success. Conventional anchoring techniques encompass a suture technique, a steri-strip application, and a manufacturer's short plastic anchor provided with trial leads. However, conventional methods and apparatus may result in lead migration. Further, the conventional methods and apparatus may lead to potential infection rate, likelihood of skin maceration in certain applications, pain, and discomfort for the patients. Additionally, the conventional methods and apparatus may include the complexity of lead management without displacing local anesthesia such as in sutures. Further, diagnosis of post-laminectomy syndrome may be correlated with increased lead migration, with no statistically significant variance observed among different anchoring techniques. Furthermore, the conventional methods and apparatus may have postulated that mitigating shear mechanical stress at the lead entry point may effectively restrict its migratory tendencies.

Consequently, there is a need for an improved medical anchoring apparatus, to address at least the aforementioned issues.

SUMMARY

This summary is provided to introduce a selection of concepts, in a simple manner, which is further described in the detailed description of the disclosure. This summary is neither intended to identify key or essential inventive concepts of the subject matter nor to determine the scope of the disclosure.

An aspect of the present disclosure provides a medical anchoring apparatus. Further, the medical anchoring apparatus may include an omega shaped anchoring element. Further, the omega shaped anchoring element may include a proximal end and a distal end. The proximal end includes a primary inlet groove for receiving at least one end of a lead. The distal end of the omega shaped anchoring element includes a stopper element and an outlet groove, for protruding the at least one end of the lead. Furthermore, the medical anchoring apparatus may include a nanosilver antimicrobial foam coupled beneath the distal end of the omega shaped anchoring element at a lead entry point of a skin area of a subject around the outlet groove for antimicrobial and absorptive capabilities. Further, the medical anchoring apparatus may include a single coated nonwoven porous acrylic adhesive, coupled beneath the omega shaped anchoring element, configured to adhere to the skin area of the subject.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure. It will be understood by those skilled in the art that the foregoing general description and the following detailed description are exemplary and explanatory of the disclosure and are not intended to be restrictive thereof.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

The terms "comprise", "comprising", or any other variations thereof, are intended to cover a non-exclusive inclusion, such that one or more devices or sub-systems or elements or structures or components preceded by "comprises a" does not, without more constraints, preclude the existence of other devices, sub-systems, additional sub-modules. Appearances of the phrase "in an embodiment", "in another embodiment" and similar language throughout this specification may, but necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

Embodiments of the present disclosure provide a medical anchoring apparatus. The present disclosure addresses the common issue of lead migration, a critical concern in spinal cord stimulation (SCS) procedures, by demonstrating minimal migration compared to conventional anchoring methods. Further, the present disclosure streamlines the anchoring process, eliminating the need for local anesthesia, and thus reducing pain and discomfort during application. The incorporation of a nanosilver antimicrobial foam enhances infection control, surpassing the efficacy of traditional soft surgical gauze. The nanosilver antimicrobial foam shows >99.99% efficacy against gram-positive, gram-negative, and fungus species.

The medical anchoring apparatus utilizes high-quality porous acrylic adhesive to promote extended wear and comfort, while also reducing the risk of skin-related complications. Furthermore, the present disclosure provides simplified lead management for patients to maintain skin hygiene without lead displacement.

Referring now to the drawings, and more particularly to FIG. 1A through FIG. 4C, where similar reference characters denote corresponding features consistently throughout the figures, there are shown preferred embodiments, and these embodiments are described in the context of the following exemplary system and/or method.

Figure 1A:
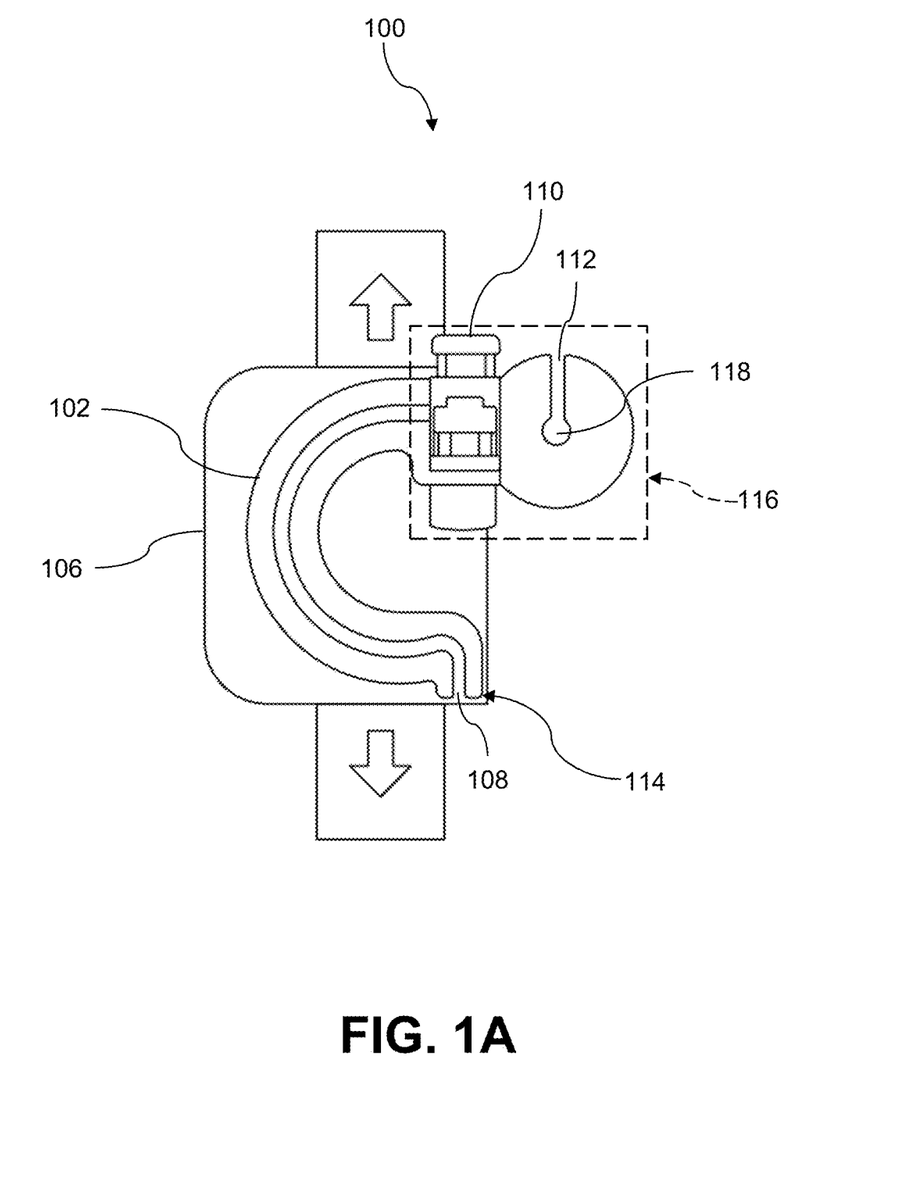
FIG. 1A illustrates an exemplary schematic diagram representation of a top view of a medical anchoring apparatus, in accordance with an embodiment of the present disclosure.
Figure 1B:
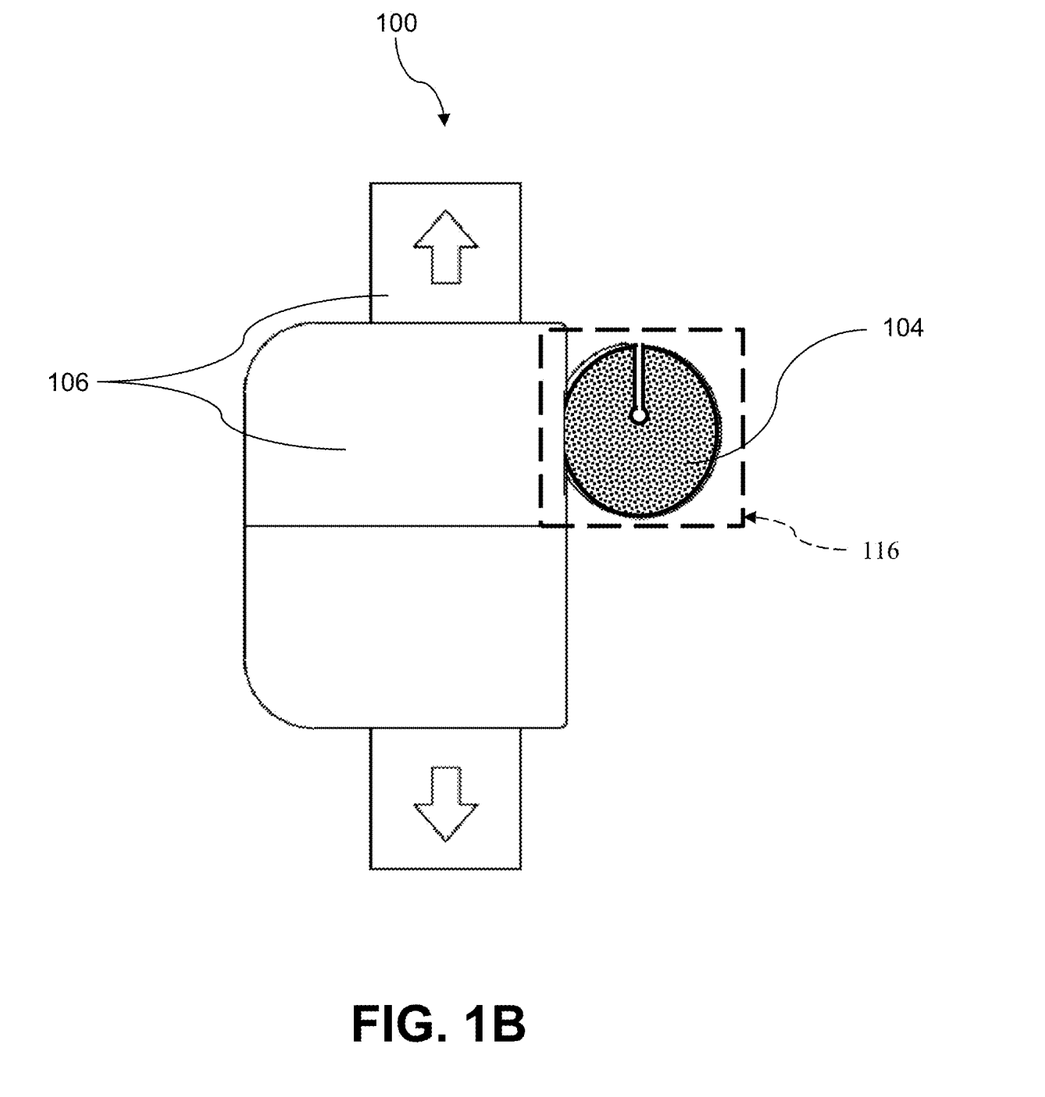
FIG. 1B illustrates an exemplary schematic diagram representation of a bottom view of the medical anchoring apparatus, in accordance with an embodiment of the present disclosure.

FIG. 1A and FIG. 1B illustrate exemplary schematic diagrams representation of a top view and a bottom view of the medical anchoring apparatus 100, in accordance with an embodiment of the present disclosure. The medical anchoring apparatus 100 may include an omega shaped anchoring element 102, a nanosilver antimicrobial foam 104, and a single coated nonwoven porous acrylic adhesive 106.

In an embodiment, the medical anchoring apparatus 100 may include the omega shaped anchoring element 102. The omega shaped anchoring element 102 may include a proximal end 114 and a distal end 116. The proximal end 114 may include a primary inlet groove 108 for receiving at least one end of a lead that has a first proximal end that inserts into an external simulator and a first distal end that is in the epidural space, where the electrodes attached to the leads are used for stimulation. Further, the component of the lead that is inserted through the skin may protrude out of the distal end 116 of the omega shaped anchoring element 102, which includes the stopper element 110 and an outlet groove 112. The stopper element 110 includes a button lock and spring that clasps a shaft of the lead to prevent movement. The button lock is actuated by a tensile force of the spring. This ensures the lead does not compress preventing electrical transmission based on a predefined tensile force. The omega shaped anchoring element 102 includes a channel. The lead passes through a channel of the omega shaped anchoring element 102. The channel diameter of omega shaped anchoring element 102 may encapsulate and house the lead and channel shape with curves with outlet at the primary inlet groove 108. This ensures an additional point of anchoring and prevention of lead migration. Further, the omega shaped anchoring element 102 may manage displacement of the lead. The distal end 116 comprises a flat-shaped element with the outlet groove 112. The lead is passed through the stopper element 110.

In an embodiment, the medical anchoring apparatus 100 may include the nanosilver antimicrobial foam 104 coupled beneath the distal end 116 of the omega shaped anchoring element 102 at a lead entry point of a skin area of a subject around the outlet groove 112. The nanosilver antimicrobial foam includes, but not limited to, silver particles to serve as an antimicrobial agent. Herein another exemplary embodiment, the nanosilver antimicrobial foam 104 has a foam density range between 6.0 lbs/ft$^3$ and 7.5 lbs/ft$^3$. This ensures that, as the lead exits or enters the skin through the outlet groove 112 at the nanosilver antimicrobial foam 104, where there is the highest chance of skin flora and infection. The nanosilver antimicrobial foam 104 may prevent skin infection. The nanosilver antimicrobial foam 104 may absorb excess body fluid, serosanguinous fluid, and blood at the lead entry point of the skin area of the subject. In addition to its antimicrobial effects the nanosilver antimicrobial foam 104 consists of unique absorptive characteristics as depicted in Table 1:

TABLE 1

Physical and absorption characteristics

| Property | Typical value |
| --- | --- |
| Foam thickness | 4.5 ± 0.5 mm |
| Foam density | 6.0-7.5 lbs/ft³ |
| Tensile strength | 160 kPa |
| Elongation at break | 225% |
| Tear strength | 290 N/m |
| Absorption rate of a water drop | Instantaneous |
| Free swell absorptive capacity | ~15 g/g |
| Fluid retention under 40 mmHg compression | ~10 g/g |

In an embodiment, the medical anchoring apparatus 100 may include the single coated nonwoven porous acrylic adhesive 106 coupled beneath the omega shaped anchoring element 102. The single coated nonwoven porous acrylic adhesive 106 may adhere to the skin area of the subject. The subject may be, but not limited to, a human, an animal, and the like. The single coated nonwoven porous acrylic adhesive 106 is configured to permit air and moisture to pass through the skin. The single coated nonwoven porous acrylic adhesive 106 may include a liner, an adhesive, and a carrier. The single-coated nonwoven may be a single-coated, white, embossed, polyester nonwoven with a porous acrylic adhesive. The single coated nonwoven porous acrylic adhesive 106 creates a high moisture vapor transmission rate (MVTR), allowing air and moisture to pass freely through the breathable adhesive and nonwoven carrier, which can support extended wear and reduce the likelihood of skin maceration in some applications.

In an embodiment, the medical anchoring apparatus 100 may include a secondary inlet groove 118 for receiving the at least one lead deviating from the primary inlet groove 108. The medical anchoring apparatus 100 may secure the at least one end of the lead with a pre-defined lead migration, and lead management.

Though a few components or elements are disclosed in FIG. 1, there may be additional components or elements that are not shown. The person skilled in the art should not be limiting the components or elements shown in FIG. 1.

Those skilled in the art will recognize that, for simplicity and clarity, the full structure and operation of all data processing systems suitable for use with the present disclosure are not being depicted or described herein. Instead, only so much of the apparatus 100 as is unique to the present disclosure or necessary for an understanding of the present disclosure is depicted and described. The remainder of the construction and operation of the apparatus 100 may conform to any of the various current implementations and practices that were known in the art.

Figure 2:
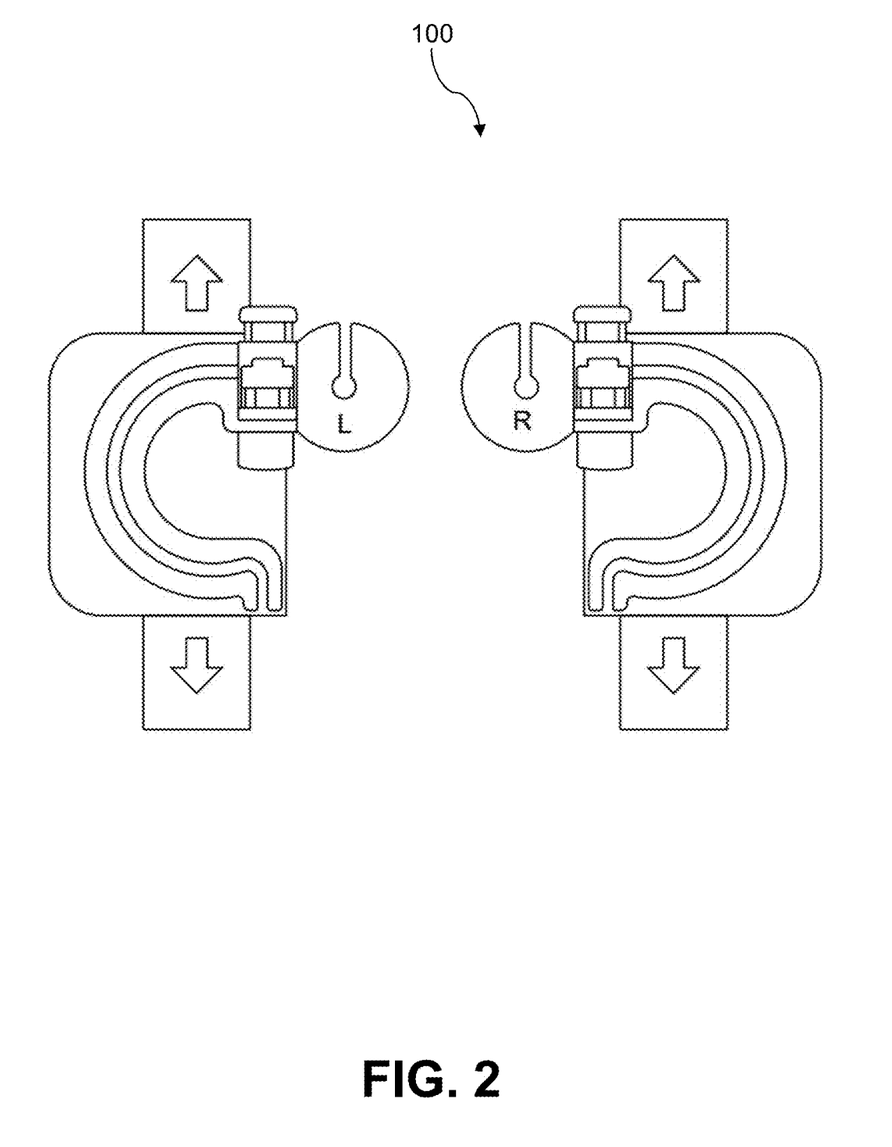
FIG. 2 illustrates an exemplary schematic diagram representation of right and left clips of a medical anchoring apparatus, in accordance with an embodiment of the present disclosure.

FIG. 2 illustrates an exemplary schematic diagram representation of right and left clips of the medical anchoring apparatus 100, in accordance with an embodiment of the present disclosure. The medical anchoring apparatus 100 comprises flexible polyurethane material for conforming to body shape and movement which allows for increased comfort and spatial positioning. The flexible polyurethane material hardness is altered by a durometer to achieve a balance for anchoring the lead in the channel while being soft to not damage skin but also contort in different shapes and bend points throughout anchoring of the medical anchoring apparatus if patients are to do activity during a trial week. The materials in the medical anchoring apparatus 100 may be magnetic resonance imaging (MRI), x-ray, and ultrasound compatible and safe. If a physician needs to image lead while the lead is anchored to the skin with the medical anchoring apparatus 100 there may be no issues. The right and left clips of the medical anchoring apparatus 100 comprise an ipsilateral, contralateral right (R), and left (L) confirmation for two lead placements during therapy.

Further, the single coated nonwoven porous acrylic adhesive 106 may be conformable, highly breathable, heat sealable, extended wear time, gamma, and Ethylene oxide (EtO) sterilizable. The single coated nonwoven porous acrylic adhesive 106 may include a liner, an adhesive, and a carrier. The carrier thickness may be, for example, 12 mils 300 μm white embossed PET nonwoven. The single coated nonwoven porous acrylic adhesive 106 thickness may be, for example, 2 mils to 50 μm porous acrylic adhesive designed for medical applications. Further, the release liner thickness may be, for example, 3.1 mils to 80 μm white single-coated kraft.

Furthermore, the product exhibits specific adhesive characteristics, including a peel adhesion of tds-01 at 0.6 lbf/in (2.5 n/25 mm) on polyethylene and tds-05 at 1.1 lbf/in (5 n/25 mm) on stainless steel. It also demonstrates liner release of tds-06 at 1.3 oz/in (39 g/25 mm), reverse tack of tds-07 at 2.5 lbf/in (11 n/25 mm), static shear of tds-12 for 20 minutes, and moisture vapor transmission rate (MVTR) of tds-16 at 129 g/100 in2 per 24 hr (2000 g/m2 per 24 hr). Moreover, the PET nonwoven has a storage and shelf life of two years when stored under conditions of 23° C. (73° F.), 50% relative humidity, away from direct sunlight, and in its original packaging.

Figure 3:
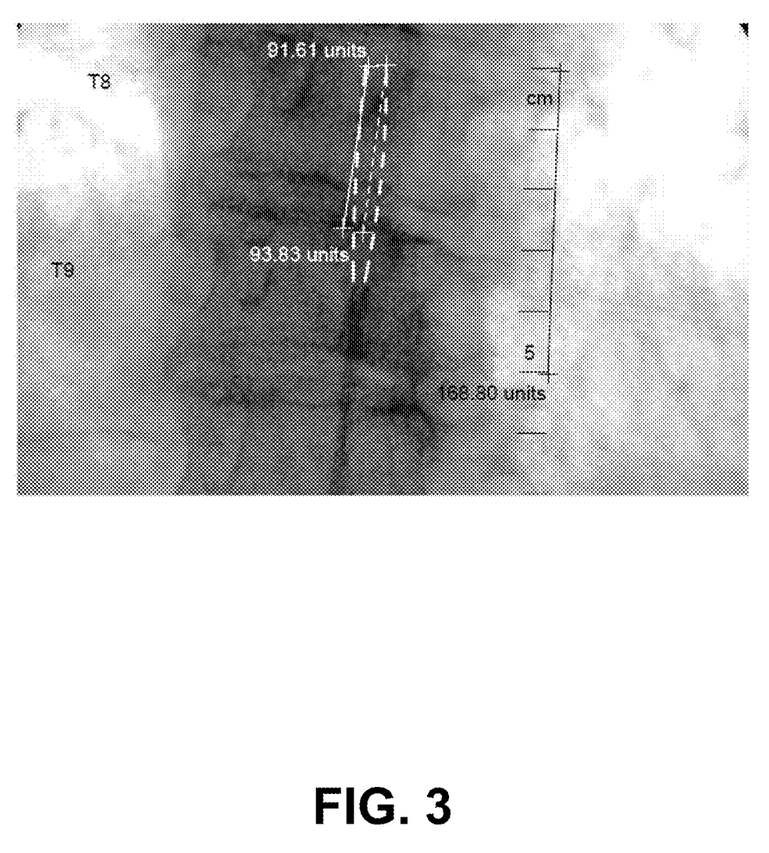
FIG. 3 illustrates an exemplary schematic diagram representation of a fluoroscopy image to measure the midline distance of a spinal cord stimulation (SCS) trial leads tipping away from the superior end plate (SEP), in accordance with an embodiment of the present disclosure.

FIG. 3 illustrates an exemplary schematic diagram representation of a fluoroscopy image to measure the midline distance of a spinal cord stimulation (SCS) trial leads tipping away from the superior end plate (SEP), in accordance with an embodiment of the present disclosure. A fluoroscopy measurements protocol may be performed by establishing an alignment of the superior vertebral body endplate (SEP) with the upper extent of the lead, designating this as our reference point for all measurements. In instances of lead migration, measurements were conducted to quantify the displacement of the electrode tip concerning the SEP. To account for variations in fluoroscopic image size compared to the actual size of the lead and the patient's vertebrae, a magnification correction calculation was applied. This correction calculation involved the placement of a radio-opaque ruler of a specific length (50 mm in this case) on each patient's skin at the lead entry site. The ruler's measured length on the fluoroscopy image may be divided by its actual length, as depicted in FIG. 3. The outcome provided the magnification correction factor necessary for the precise determination of lead movement. Each lead's migration and positional shifts were assessed in a vertical orientation to ensure accurate monitoring and measurement.

Figure 4A:
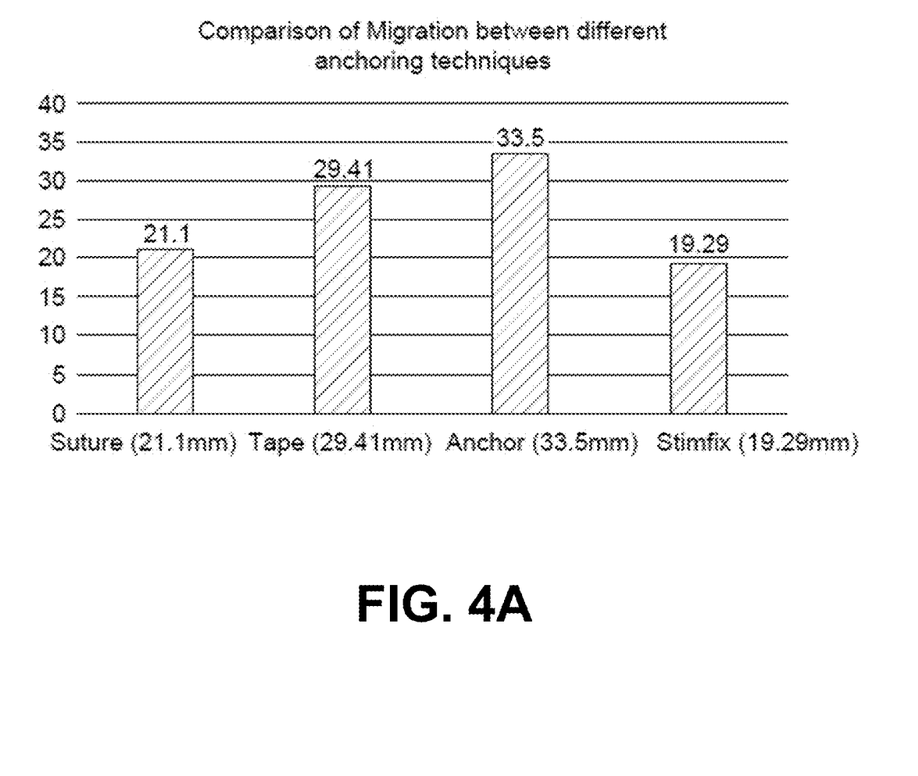
FIG. 4A illustrates an exemplary graph diagram representation of a migration of different anchoring techniques and a depiction of the results of medical anchoring apparatus related migration versus suture tape and manufacturers' anchor, in accordance with an embodiment of the present disclosure.

FIG. 4A illustrates an exemplary graph diagram representation of a migration of different anchoring techniques and a depiction of the results of medical anchoring apparatus related migration versus suture tape and manufacturers' anchor, in accordance with an embodiment of the present disclosure. The study may primarily be compared for average migration rates observed with conventional anchoring techniques to the medical anchoring apparatus 100 trail lead focusing on raw data in the interim analysis. Results of the raw data may have shown that the medical anchoring apparatus 100 has demonstrated significantly less average migration than other methods, which is depicted in a bar graph of FIG. 4A.

Consider group 1 which has twenty-eight individuals of age 27 or older who are scheduled for a 7-day percutaneous SCS trial enrolled in the study. Individuals are assigned to one of three lead anchoring groups: nine with manufacturer anchor, ten with adhesive tape alone, and nine with a simple suture technique. Fluoroscopy was used to determine the position of the lead, and images were taken on the following time points, Days 1, 3, and 7 before the lead removal. A standardized fluoroscopy measurement protocol was used to measure the lead migration. Further, consider group 2, which has eighteen individuals who were prospectively enrolled under lead anchoring placement using the medical anchoring apparatus 100. A total of 36 leads were anchored with the medical anchoring apparatus 100. Fluoroscopy images may be obtained at the following time points: On day 1, after the procedure and the medical anchoring apparatus 100 placement, an image was taken in lateral decubitus position post flexion, which is taken as a baseline and compared to the image taken before the lead removal on the seventh day (D7) of post-trial follow-up. Lead migration is assessed by standardized fluoroscopy measurement protocol.

The study compares the results of two groups. The participants were separated into two distinct groups. Group 1 consists of twenty-eight individuals from a single center who are randomly assigned to one of the three traditional anchoring techniques. Group II enrolled a total of eighteen individuals from four different pain clinics for the STIMFIX™ lead anchoring technique. Group 1: It is a Randomized, Open-Label, Single-Centered Trial. A total of twenty-eight participants, including eleven males and seventeen females, ranged in age from 27 to 84. Individuals are assigned randomly to one of three lead anchoring techniques: suture, tape, or manufacturer anchor. All patients have undergone the SCS trial with Boston Scientific. Images were captured on day one after the procedure and on day seven before the lead removal. Lead migration is measured by comparing the two images and using a standardized fluoroscopy measurement protocol.

Further, group II: This is a WIRB-approved, multi-center, open-label, non-randomized, single-arm study. Consent was obtained from everyone who participated in the study. While screening, individuals with severe allergies to adhesives were excluded. In total, 18 people participated in this interim analysis, including 7 males and 11 females. Five individuals were implanted with Medtronic SCS trail and thirteen with Boston Scientific. Image-1 was captured on Day 1 following the procedure and STIMFIX™ placement with the patient in the lateral decubitus position for flexion, and Image-2 was captured on Day 7 before the lead removal. Lead migration is measured by comparing the two images and using a standardized fluoroscopy measurement protocol.

In the study, (group-I) reported more migration with manufacturer's anchors (33.5 mm) than with tape-only (Steri-Strip) (29.41 mm) or suturing procedures (21.1 mm), whereas (group-II) experienced an average migration of (19.29 mm) using the medical anchoring apparatus 100 anchoring technology. Patients reported no reduction in efficacy or loss of paresthesia coverage during the trial period. No lead revisions have been noted.

Figure 4B:
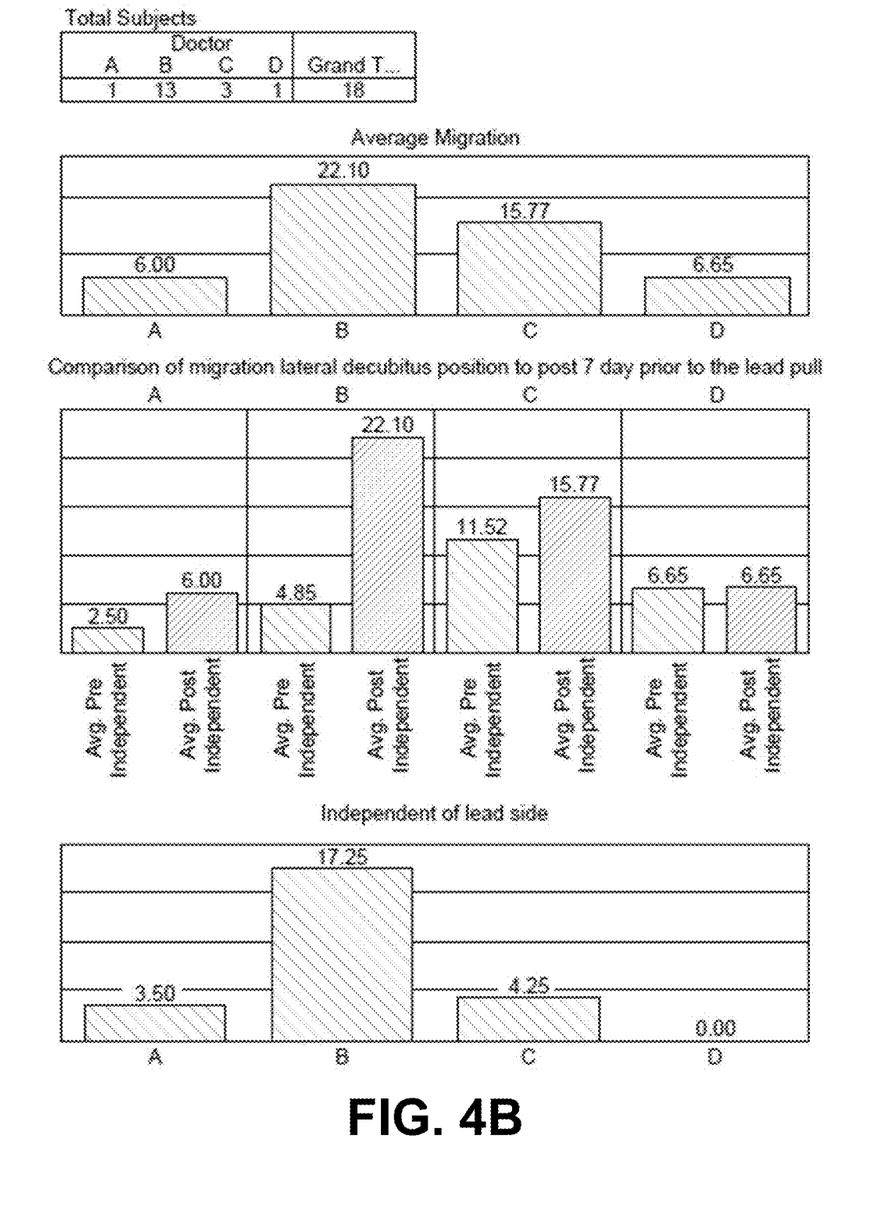
FIG. 4B illustrates an exemplary graph diagram representation of average migration, comparison, and independent of lead side, at each site, in accordance with an embodiment of the present disclosure.

FIG. 4B illustrates an exemplary graph diagram representation of average migration, comparison, and independent of lead side, at each site, in accordance with an embodiment of the present disclosure. FIG. 4B includes three distinct descriptions at each site a) average migration b) comparison and c) independent of lead side. In the upper left corner, the number of participants from each center who participated in this study is displayed. The average migration, the Top row depicts the average migration from four different sites, which are named A, B, C, and D, regardless of the lead laterality. The comparison, second set of bar graphs depicts a comparison of migration from lateral decubitus position to post seven days before the lead pull. Average pre-independent refers to the average migration when the patient is lying in a lateral decubitus position after the lead is implanted, whereas post independent indicates the average migration in each center that was observed. On the $7^{th}$ day, follow up before the lead pulls. The independent lead side is the difference between the migration observed on the trial day to post-trial follow-up.

As the image taken in the lateral decubitus position served as a baseline for comparing the migration on day 7 post-lead removal, the following is the difference in migration between the four individual centers. Center A measured 3.50 mm, Center B measured 17.25 mm, Center C measured 4.25 mm, and Center D measured zero migration. The disparity in results may likely be due to the fact that enrollment in center B is significantly higher than in centers A, C, and D, with an account for individual provider variability. In addition, the left lead has migrated more frequently than the right lead. Again, this may be an early interim result that requires further exploring to determine whether this finding is incidental or whether this finding requires further exploration.

Figure 4C:
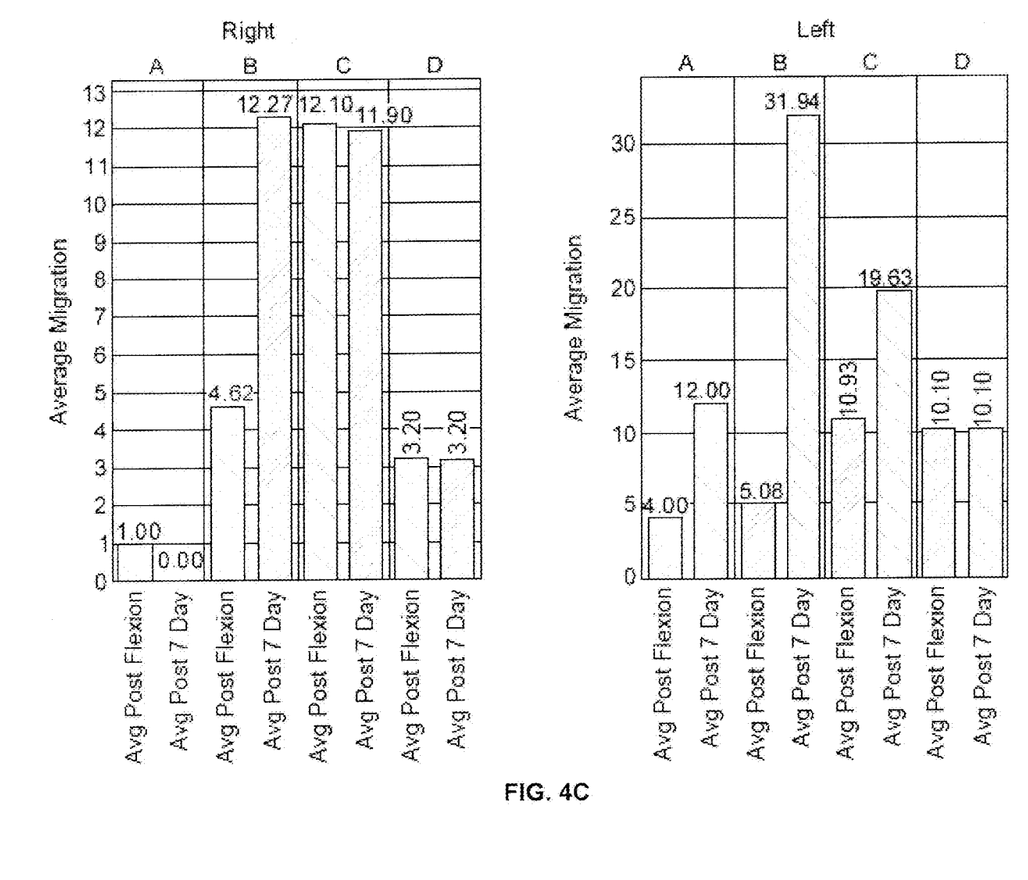
FIG. 4C illustrates an exemplary graph diagram representation of average migration from individual sites specific to lead laterality, in accordance with an embodiment of the present disclosure.

FIG. 4C illustrates an exemplary graph diagram representation of average migration from individual sites specific to lead laterality, in accordance with an embodiment of the present disclosure. A bar graph indicating the average migration of an individual lead side is depicted in FIG. 4C. The left side of FIG. 4C demonstrates right lead migration at four different sites, and the right side of the figure demonstrates the left lead migration at four different sites. The comparison is based on the baseline-migration observed during the lateral decubitus position on the trial day, which is noted as average post flexion to the migration that is observed on the $7^{th}$-day follow-up. Moreover, no significant adverse events were reported except for one participant noted to have skin abrasion after the medical anchoring apparatus 100 removal. There was no statistical analysis performed within group II to present raw data comparisons.

Further, Table 2 below depicts one or more parameters included in the study. Gender and vendor specific parameters were specifically included in the study sub analysis whereas age and diagnosis were excluded in the sub-analysis.

TABLE 2

| Parameter | STIMFIX ™(N = 18) |
|---|---|
| Gender | Males: 7 |
|  | Females: 11 |
| Age | Mean age: 77 |
| Diagnosis | Complex regional pain syndrome: N (3) |
|  | Post laminectomy syndrome: N (7) |
|  | Lumbar radiculopathy: N (7) |
|  | Other chronic pain syndromes: N (1) |
| Vendor-specific | Medtronic: 5 |
|  | Boston Scientific: 13 |

Furthermore, Table 3 below depicts the effects of the medical anchoring apparatus 100. As demonstrated, one subject has experienced the skin abrasion which is classified as Grade-1 AE, and the rest of the expected events were reported to be none.

TABLE 3

| Adverse Events (AE) | Number of subjects (N) |
|---|---|
| Medical Device site pain | None Reported |
| Bleeding | None Reported |
| Infection | None Reported |
| Itching | None Reported |
| Allergic reactions | None Reported |
| Skin Abrasion | 1 (N1) 5.5% |

Additionally, Table 4 below shows the results of a physician survey questionnaire shown in this comparative table. As shown in the table, the survey questionnaire contrasted the ease of use and other aspects of standard anchoring techniques versus the medical anchoring apparatus 100. Each parameter was rated on a scale of 0 to 10, with 0 being the most difficult to use and 10 being the easiest. All four independent pain practices gave the medical anchoring apparatus 100 an average rating of 9.25/10 for ease of use. Aside from the ease of use, choosing the medical anchoring apparatus 100 over other anchoring methods and recommending the medical anchoring apparatus 100 to colleagues has a similar average value. Furthermore, as seen in the last column, the study took physicians' descriptions into account when describing issues with each anchoring approach.

TABLE 4

| | Parameters | | | | | | | |
|---|---|---|---|---|---|---|---|---|
| | A | | | | B | | | |
| Anchoring Technique | Suture | Suture + Manufacturers Anchor | Steri-Strip | STIMFIX | Suture | Suture + Manufacturers Anchor | Benzoin + Steri-Strip | STIMFIX |
| Applicability or Ease of Use | 0 | 0 | 4 | 10 | 10 | N/A | 10 | 8 |
| Average time taken for Performing Anchoring Techniques | 5-7 minutes | 5-7 minutes | 2-3 minutes | 0-15 secs | 5-10 minutes | N/A | <1 minute | 0-15 secs |
| Choosing Conventional VS STIMFIX | 0 | 0 | 0 | 10 | 1 | N/A | 7 | 8 |
| Recommending Stimfix to Colleagues | | | | 10 | | N/A | | 8 |
| Challenges encountered with Anchoring techniques | "Takes significantly more time, is more invasive, and requires local anesthesia/ sedation for comfort" | "Similar to suture it takes significantly more time, is more invasive, and requires local anesthesia/ sedation for comfort" | "It's very sticky and difficult to handle" "Often does not seal well to the lead" "Sticks to gloves and can sometimes pull the leads inadvertently" "When contacted with heme, it does often peel off and is rendered useless" | "Pressing the lead into the groove took few attempts" | "Takes longer, requires more local anesthetic" | "N/A" | "Migration of leads, steri strips may come off secondary to perspiration" | "Pressing the lead into the final anchoring curve can be tricky" |

| | Parameters | | | | | | | |
|---|---|---|---|---|---|---|---|---|
| | C | | | | D | | | |
| Anchoring Technique | Suture | Suture + Manufacturers Anchor | Steri-Strip, 2 × 2 Gauze, 5 × 7 tegaderm | STIMFIX | Suture | Suture + Manufacturers Anchor | Steri-Strip | STIMFIX |
| Applicability | 3 | 3 | 6 | 10 | 5 | 5 | 3 | 9 |
| Average time taken for Performing Anchoring Techniques | 2 minutes | 2 minutes | 3 minutes | 0-15 secs | 3-4 minutes | 3-4 minutes | 5-6 minutes | 0-15 secs |
| Choosing Conventional VS STIMFIX | | | 2 | 10 | 2 | 2 | 2 | 9 |

TABLE 4-continued

| | | | | | | | | |
|---|---|---|---|---|---|---|---|---|
| Recommending STIMFIX ™ to Colleagues | 0 | 0 | | 10 | | | | 10 |
| Challenges encountered with Anchoring techniques | "Pain for patient. Skin irritation and atrophy" | "More tedious and more pain." | "Struggle to keep the strain loops down while steri stripping them down" | "No Significant challenges encountered" | "Increased Pain and itching at the Suture Site" Noticed erythema at the suture Site" | "Similar to suture increased pain at the suture site" | "Lead migration during taping" "Tape/Steri-Strips falling off" | "No Significant challenges encountered" |

Results: Interim Analysis has found that the average migration of the medical anchoring apparatus 100 may be, for example, 19.29 millimeters, compared to 21.1 millimeters for sutures, 29.4 millimeters for tape, and 33.5 millimeters for manufacturer anchors. A one-way analysis of variance (ANOVA) analysis within group 1 may demonstrate no significant difference between the three commonly used anchoring techniques (p=0.404), Group 1 and Group 2 raw data were presented for comparison. In addition, no major adverse events were reported within Group II. During the post-trial period, percutaneous trail lead migrates, with inferior migration occurring most frequently. Lead anchoring techniques play a major role in reducing lead migration. Compared to suture, tape, and manufacturer anchors, a novel, non-invasive medical anchoring apparatus 100 lead anchoring technique has demonstrated promising results with minimal lead migration and the added benefit of improving providers' efficiency.

Group 1: Study results found that all leads migrated inferiorly. During the 7-day trial, the lead migration with the manufacturer anchor was 33.35 mm (SD=31.24); while the tape was 29.41 mm (SD=16.94); and the suture was 21.10 mm (SD=24.15). A one-way ANOVA revealed no significant difference between the conventional techniques (P=0.404). Group 2: medical anchoring apparatus 100 demonstrated an average migration of 19.29 mm compared to conventional methods in group 1.

The SCS is one of the most commonly opted therapies in failed back surgery syndrome, complex regional pain syndrome, peripheral neuropathy, and peripheral ischemic limb pain. (5). Prior to implanting permanent SCS, patients will undergo a trial phase lasting anywhere between 3 to 30 days. (5). In the trial phase, participants record their pain levels during daily activities. Conversion to the permanent SCS device significantly depends on the pain reduction from baseline. Ideally, the improvement should exceed 50% of the baseline pain score (5). The conversion rate to permanent implants can be influenced by the loss of therapeutic efficacy, which is commonly caused by lead migrations (6). Lead migration is the unintentional displacement of SCS leads within the epidural space, which can occur when the mechanical stress overcomes the anchoring forces (7, 8). Current research indicates that lead migration rates range from 2.1% to 27% [2, 8, 9-14]. Despite the fact that there are numerous risk factors for lead migration, such as physician's experience, premature return to their activity, lead entry point, location of the leads, and anchoring techniques (2), there is a paucity of evidence to support the effectiveness of anchoring techniques (14).

In addition, a physician survey may be conducted in four different independent interventional pain practices. Physicians have reported overall average rating for the medical anchoring apparatus 100 applicability is 9.25/10, and a similar average has been noticed on the following two parameters 1) Choosing the medical anchoring apparatus 100 over other anchoring methods and recommending the medical anchoring apparatus 100 to other providers. The average time spent on the medical anchoring apparatus 100 anchoring method is noticed to be 10-15 seconds by all four physicians reflecting improved providers' efficiency. Clinicians have highlighted the ease of application, which eliminates the need for local anesthesia compared to sutures, and reduction in pain and discomfort for the patients. The prospective interim investigation of the medical anchoring apparatus 100 anchoring technology revealed promising outcomes. Furthermore, multi-center trials with larger cohorts are required to explore and support these findings.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

A description of an embodiment with several components in communication with each other does not imply that all such components are required. On the contrary, a variety of optional components are described to illustrate the wide variety of possible embodiments of the invention. When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of more than one device or article, or a different number of devices/articles may be used instead of the shown number of devices or programs. The functionality and/or the features of a device may be alternatively embodied by one or more other devices that are not explicitly described as having such functionality/features. Thus, other embodiments of the invention need not include the device itself.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having,"

"containing," and "including," and other similar forms are intended to be equivalent in meaning and be open-ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limited, of the scope of the invention, which is outlined in the following claims.

The invention claimed is:

1. A medical anchoring apparatus for managing lead migration, comprising:
   an omega shaped anchoring element, comprising a proximal end and a distal end, the proximal end comprises a primary inlet groove for receiving at least one end of a lead, and the distal end of the omega shaped anchoring element comprises a stopper element and an outlet groove, for protruding the at least one end of the lead, wherein the omega shaped anchoring element comprises a channel exhibiting a curved shape, wherein the lead passes through the channel of the omega shaped anchoring element;
   a nanosilver antimicrobial foam coupled beneath the distal end of the omega shaped anchoring element at a lead entry point of a skin area of a subject around the outlet groove; and
   a single coated nonwoven porous acrylic adhesive, coupled beneath the omega shaped anchoring element, configured to adhere to the skin area of the subject, wherein the single coated nonwoven porous acrylic adhesive includes a liner, an adhesive, and a carrier, with an optimal moisture vapor transmission rate (MVTR),
   the medical anchoring apparatus is configured to manage at least one of a: pre-defined lead migration and lead management of the lead associated with an electrode.

2. The medical anchoring apparatus of claim 1, wherein the distal end further comprises:
   a secondary inlet groove for receiving the at least one end of the lead deviating from the primary inlet opening.

3. The medical anchoring apparatus of claim 1, wherein the single coated nonwoven porous acrylic adhesive is configured to permit air and moisture to pass through the skin.

4. The medical anchoring apparatus of claim 1, wherein the omega shaped anchoring element is configured to manage displacement of the lead and the electrode.

5. The medical anchoring apparatus of claim 1, wherein the nanosilver antimicrobial foam comprises silver particles.

6. The medical anchoring apparatus of claim 1, wherein the lead and the electrode is configured to migrate through the skin of the subject to a body of the subject.

7. The medical anchoring apparatus of claim 1, wherein the distal end comprises a flat-shaped element with the outlet groove.

8. The medical anchoring apparatus of claim 1, wherein the lead is passed through the stopper element.

9. The medical anchoring apparatus of claim 1, wherein the lead comprises a first proximal end and a first distal end,
   the first proximal end is inserted into an external simulator with the electrode for stimulation; and
   the first distal end is positioned within an epidural space.

10. The medical anchoring apparatus of claim 1, wherein the stopper element includes a button lock and spring to clasps a shaft associated with the at least one end of the lead to prevent movement.

11. The medical anchoring apparatus of claim 10, wherein the button lock is actuated by a tensile force of the spring.

12. The medical anchoring apparatus of claim 1, wherein the materials of the medical anchoring apparatus is magnetic resonance imaging (MRI), x-ray, and ultrasound compatible and safe.

13. The medical anchoring apparatus of claim 1, wherein the channel diameter of omega shaped anchoring element may encapsulate and house the lead,
   the channel exhibits curved shapes that ultimately lead to an outlet located at the primary inlet groove.

14. The medical anchoring apparatus of claim 1, wherein the nanosilver antimicrobial foam may absorb at least one of: excess body fluid, serosanguinous fluid, and blood at the lead entry point of the skin area of the subject.

15. The medical anchoring apparatus of claim 1, wherein the medical anchoring apparatus is configured with a flexible polyurethane material for conforming to body shape and movement which allows for increased comfort and spatial positioning,
   wherein the flexible polyurethane material hardness is altered by a durometer to achieve a balance for anchoring the lead in the channel,
   wherein the flexible polyurethane material is provided with an optimized softness to prevent damage to the skin,
   wherein the flexible polyurethane material configured to contort in different shapes and bend points throughout anchoring of the medical anchoring apparatus.

16. The medical anchoring apparatus of claim 1, wherein the primary inlet groove is in a cylindrical shape.

17. The medical anchoring apparatus of claim 1, comprises an ipsilateral, contralateral right (R), and left (L) confirmation for the two lead placements during therapy.

* * * * *